(12) United States Patent
Forsberg et al.

(10) Patent No.: US 12,071,282 B2
(45) Date of Patent: Aug. 27, 2024

(54) SYSTEM AND METHOD FOR PACKAGING A BIOPROCESSING BAG AND ASSOCIATED COMPONENTS, AND PACKAGING FOR A BIOPROCESSING BAG

(71) Applicant: GLOBAL LIFE SCIENCES SOLUTIONS USA LLC, Marlborough, MA (US)

(72) Inventors: Steven Forsberg, West Boylston, MA (US); Ralph Stankowski, Westborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 0 days.

(21) Appl. No.: 17/990,079

(22) Filed: Nov. 18, 2022

(65) Prior Publication Data

US 2023/0082880 A1    Mar. 16, 2023

Related U.S. Application Data (63) Continuation of application No. 16/729,859, filed on Dec. 30, 2019, now Pat. No. 11,535,421.

(51) Int. Cl.
| | | |
|---|---|---|
| B65D 5/50 | (2006.01) | |
| A61L 2/08 | (2006.01) | |
| A61L 2/26 | (2006.01) | |
| B65B 5/04 | (2006.01) | |
| B65B 61/14 | (2006.01) | |
| B65D 33/06 | (2006.01) | |
| C12M 1/00 | (2006.01) | |

(52) U.S. Cl.
CPC .............. *B65D 5/503* (2013.01); *A61L 2/081* (2013.01); *A61L 2/26* (2013.01); *B65B 5/04* (2013.01); *B65B 61/14* (2013.01); *B65D 33/06* (2013.01); *C12M 23/14* (2013.01); *C12M 23/26* (2013.01); *A61L 2202/182* (2013.01)

(58) Field of Classification Search
CPC ......... B65D 5/503; B65D 33/06; A61L 2/081; A61L 2/26; A61L 2202/182; B65B 5/04; B65B 61/14; C12M 23/14; C12M 23/26; C12M 27/02

See application file for complete search history.

(56) References Cited

U.S. PATENT DOCUMENTS

| | | | | |
|---|---|---|---|---|
| 4,290,300 A | * | 9/1981 | Carver ................... | G01N 9/12 73/32 R |
| 4,727,040 A | * | 2/1988 | Freedman .............. | C12M 29/00 435/295.3 |
| 8,741,631 B2 | * | 6/2014 | Le .......................... | B01F 33/45 366/279 |
| 9,044,718 B2 | * | 6/2015 | Ludwig ............... | B01F 27/2121 |
| 9,670,446 B2 | * | 6/2017 | Khan ..................... | C12N 5/00 |
| 9,687,852 B2 | | 6/2017 | Seal et al. | |

(Continued)

FOREIGN PATENT DOCUMENTS

CN           201817470           5/2011

*Primary Examiner* — Dariush Seif (74) *Attorney, Agent, or Firm* — Grogan, Tuccillo & Vanderleeden LLP (57) ABSTRACT

A packaging for a bioprocessing bag includes a housing having an open interior space, and a support base attached to an external side of the housing, the support base having a recess for receiving an impeller base plate of a bioprocessing bag.

18 Claims, 12 Drawing Sheets

(56) References Cited

U.S. PATENT DOCUMENTS

| | | | |
|---|---|---|---|
| 2005/0078552 A1* | 4/2005 | Zambaux | B01F 35/513 366/241 |
| 2005/0272146 A1* | 12/2005 | Hodge | B01F 35/513 435/289.1 |
| 2006/0092761 A1* | 5/2006 | Terentiev | C12M 23/14 366/314 |
| 2006/0131765 A1* | 6/2006 | Terentiev | B01F 33/00 261/93 |
| 2008/0068920 A1* | 3/2008 | Galliher | B01F 23/231 239/66 |
| 2008/0139865 A1* | 6/2008 | Galliher | C12M 41/14 588/249 |
| 2009/0035856 A1* | 2/2009 | Galliher | C12M 29/00 435/294.1 |
| 2009/0130704 A1* | 5/2009 | Gyure | C12M 39/00 435/292.1 |
| 2009/0233334 A1* | 9/2009 | Hildinger | C12P 21/02 435/235.1 |
| 2009/0303829 A1* | 12/2009 | Muecke | C12M 29/08 366/101 |
| 2009/0323466 A1* | 12/2009 | Vanhamel | B01F 35/513 366/341 |
| 2010/0255526 A1* | 10/2010 | Braet | C12M 23/14 435/29 |
| 2011/0203995 A1* | 8/2011 | Persson | B01F 27/811 210/683 |
| 2011/0207218 A1* | 8/2011 | Staheli | C12M 27/02 435/296.1 |
| 2011/0310696 A1* | 12/2011 | Goodwin | C12M 23/14 366/197 |
| 2012/0015391 A1* | 1/2012 | Zhang | C12M 27/02 435/29 |
| 2012/0171718 A1* | 7/2012 | Le | B01F 33/453 210/512.3 |
| 2012/0175012 A1* | 7/2012 | Goodwin | B01F 27/2121 141/11 |
| 2012/0241447 A1* | 9/2012 | Starnes | B65D 77/061 220/531 |
| 2012/0252108 A1* | 10/2012 | Niazi | B01F 35/513 435/284.1 |
| 2012/0284991 A1* | 11/2012 | Kusz | A61M 39/12 137/315.01 |
| 2013/0288346 A1* | 10/2013 | Tuohey | C12M 23/28 435/287.1 |
| 2015/0117142 A1* | 4/2015 | Staheli | B01F 27/191 366/279 |
| 2015/0125930 A1* | 5/2015 | Gebauer | B01F 33/45 366/342 |
| 2015/0138913 A1* | 5/2015 | Jones | B01F 35/43 366/185 |
| 2015/0151261 A1* | 6/2015 | Isailovic | C12M 27/02 366/331 |
| 2015/0151892 A1* | 6/2015 | Corten | B01F 33/453 366/273 |
| 2015/0265958 A1* | 9/2015 | Brown | B01F 23/2312 |
| 2015/0265988 A1* | 9/2015 | Williams | B01F 35/513 366/204 |
| 2015/0367302 A1* | 12/2015 | Gebauer | B01F 35/413 366/274 |
| 2016/0095279 A1* | 4/2016 | Brown | C12M 23/46 47/66.7 |
| 2016/0296897 A1* | 10/2016 | Marshall | C12M 27/02 |
| 2016/0303567 A1* | 10/2016 | Seal | C12M 23/14 |
| 2017/0107471 A1* | 4/2017 | Forsberg | C12M 29/06 |
| 2017/0183617 A1* | 6/2017 | Jones | C12N 1/00 |
| 2017/0349874 A1* | 12/2017 | Jaques | C12M 23/28 |
| 2017/0369828 A1* | 12/2017 | Mietzner | C12M 23/02 |
| 2018/0010082 A1* | 1/2018 | Jaques | B01F 27/86 |
| 2018/0057783 A1* | 3/2018 | Paldus | C12M 29/18 |
| 2018/0117546 A1* | 5/2018 | Hurd | B01F 27/2121 |
| 2018/0119084 A1* | 5/2018 | Tuohey | A61L 2/081 |
| 2018/0155667 A1* | 6/2018 | Stobbe | C12M 29/18 |
| 2019/0048303 A1* | 2/2019 | Maggiore | B67D 3/0022 |
| 2019/0218496 A1* | 7/2019 | Brau | C12M 23/58 |
| 2019/0292506 A1* | 9/2019 | Kronenberg | B01F 27/88 |
| 2019/0366286 A1* | 12/2019 | Mead | C12M 23/26 |
| 2019/0367859 A1* | 12/2019 | Gagne | B01F 35/7544 |
| 2020/0102204 A1* | 4/2020 | Saukkonen | C12M 23/14 |
| 2020/0377841 A1* | 12/2020 | Damren | C12M 33/04 |
| 2021/0016287 A1* | 1/2021 | Tuohey | C12M 37/00 |
| 2021/0024867 A1* | 1/2021 | Maggiore | C12M 23/14 |
| 2021/0138219 A1* | 5/2021 | Stankowski | C12M 29/08 |
| 2021/0198002 A1* | 7/2021 | Forsberg | B65D 5/503 |
| 2021/0222103 A1* | 7/2021 | Martin | C12M 23/24 |
| 2022/0234012 A1* | 7/2022 | Castan | B01F 27/113 |
| 2022/0251496 A1* | 8/2022 | Griffin | C12M 23/58 |
| 2023/0082880 A1* | 3/2023 | Forsberg | A61L 2/26 |

\* cited by examiner

SYSTEM AND METHOD FOR PACKAGING A BIOPROCESSING BAG AND ASSOCIATED COMPONENTS, AND PACKAGING FOR A BIOPROCESSING BAG

CROSS-REFERENCE TO RELATED APPLICATION

This application is a continuation application of, and claims the benefit of, U.S. application Ser. No. 16/729,859, filed on Dec. 30, 2019, which is hereby incorporated by reference herein in its entirety.

BACKGROUND

Technical Field

Embodiments of the invention relate generally to bioprocessing systems and methods and, more particularly, to a system and method for packaging a flexible bioprocessing bag and associated components, and packaging for such a bioprocessing bag and associated components.

Discussion of Art

A variety of vessels, devices, components and unit operations are known for carrying out biochemical and/or biological processes and/or manipulating liquids and other products of such processes. In order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

Indeed, various industries, including in the biopharmaceutical industry, single use or disposable containers are often used. In the biopharmaceutical industry, such containers can be flexible or collapsible plastic bags that are supported by an outer rigid structure such as a stainless steel shell or vessel. Use of sterilized disposable bags eliminates time-consuming step of cleaning of the vessel and reduces the chance of contamination. The bag may be positioned within the rigid vessel and filled with the desired fluid for mixing. An agitator assembly disposed within the bag is used to mix the fluid. Existing agitators are either top-driven (having a shaft that extends downwardly into the bag, on which one or more impellers are mounted) or bottom-driven (having an impeller disposed in the bottom of the bag that is driven by a magnetic drive system or motor positioned outside the bag and/or vessel). Most magnetic agitator systems include a rotating magnetic drive head outside of the bag and a rotating magnetic agitator (also referred to in this context as the "impeller") within the bag. The movement of the magnetic drive head enables torque transfer and thus rotation of the magnetic agitator allowing the agitator to mix a fluid within the vessel.

Depending on the fluid being processed, the bioreactor system may include a number of fluid lines and different sensors, probes and ports coupled with the bag for monitoring, analytics, sampling, and liquid transfer. For example, a harvest port is typically located at the bottom of the disposable bag and the vessel, and allows for a harvest line or drain tubing to be connected to the bag for harvesting and draining of the bag. In addition, existing bioreactor systems typically utilize spargers for introducing a controlled amount of a specific gas or combination of gases into the bioreactor. A sparger outputs small gas bubbles into a liquid in order to agitate and/or dissolve the gas into the liquid, or for carbon dioxide stripping. The delivery of gas via spargers helps in mixing a substance, maintaining a homogenous environment throughout the interior of the bag, and is sometimes essential for growing cells in a bioreactor. Ideally, the spargers and the agitator are in close proximity to ensure optimal distribution of the gases throughout the container.

These flexible, single-use bioprocessing bags can vary in size from a few liters up to several thousand liters and include the various ports, tubing, connectors and other components mentioned above necessary to allow for mixing, sparging, draining, sampling and sensing/measurement of the contents of the bag. As will be appreciated, such bags are therefore quite large and cumbersome, and can be unwieldy to handle, transport, inspect and install. Currently, existing bioprocessing bags and associated components are packaged in bubble wrap, which does not allow for easy inspection of the bag before installation.

In view of the above, there is a need for a system and method for packaging a flexible bioprocessing bag and associated components, and packaging for such a bioprocessing bag and associated components, which reduces the amount of bubble wrap used, allows for quick and easy inspection of the bag, and facilitates transport and installation of the bag.

BRIEF DESCRIPTION

In an embodiment, a packaging for a bioprocessing bag is provided. The packaging includes a housing having an open interior space, and a support base attached to an external side of the housing, the support base having a recess for receiving an impeller base plate of a bioprocessing bag.

In another embodiment, a kit is provided. The kit includes a flexible bioprocessing bag having an impeller base plate for receiving an impeller, and a packaging having a housing having an open interior space and a support base attached to an external side of the housing. The impeller base plate and drain tubing of the bioprocessing bag are received in a recess in the support base.

In yet another embodiment, a method of packaging a bioprocessing bag is provided. The method includes the steps of positioning drain tubing and an impeller base plate of a flexible bioprocessing bag in a recess in a support base, the support base being attached to a housing have an open interior space, positioning at least one component of the flexible bioprocessing bag in the open interior space of the housing, and coupling a handle to the flexible bioprocessing bag adjacent to a top of the flexible bioprocessing bag.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems. As used herein, the term "bag" means a flexible or semi-rigid container or vessel used, for example, as a bioreactor or mixer for the contents within.

While the embodiments described herein disclose packaging for a single-use, flexible bioreactor bag for use in bioprocessing operations, it is contemplated that the system and packaging disclosed herein may likewise be utilized for packaging and transporting flexible bags for use in a variety of industries and end uses.

Embodiments of the invention provide packaging for a flexible bioprocessing bag, and a kit including a flexible bioprocessing bag and its associated components, and packaging for such a bag. The kit includes a flexible bioprocessing bag having an impeller base plate for receiving an impeller, and a packaging having a housing having an open interior space and a support base attached to an external side of the housing. The impeller is a bottom-driven impeller (which does not utilize a long shaft extending through the bag). The impeller base plate and drain tubing of the bioprocessing bag are received in a recess in the support base. The bioprocessing bag includes sparge tubing, wherein the sparge tubing is positioned in the open interior space. The bioprocessing bag also includes a plurality of clips configured to facilitate hanging of the bioprocessing bag from a lift assembly of a bioreactor vessel, and the packaging includes a handle member configured for selective coupling to the bioprocessing bag via the plurality of clips.

Figure 1:
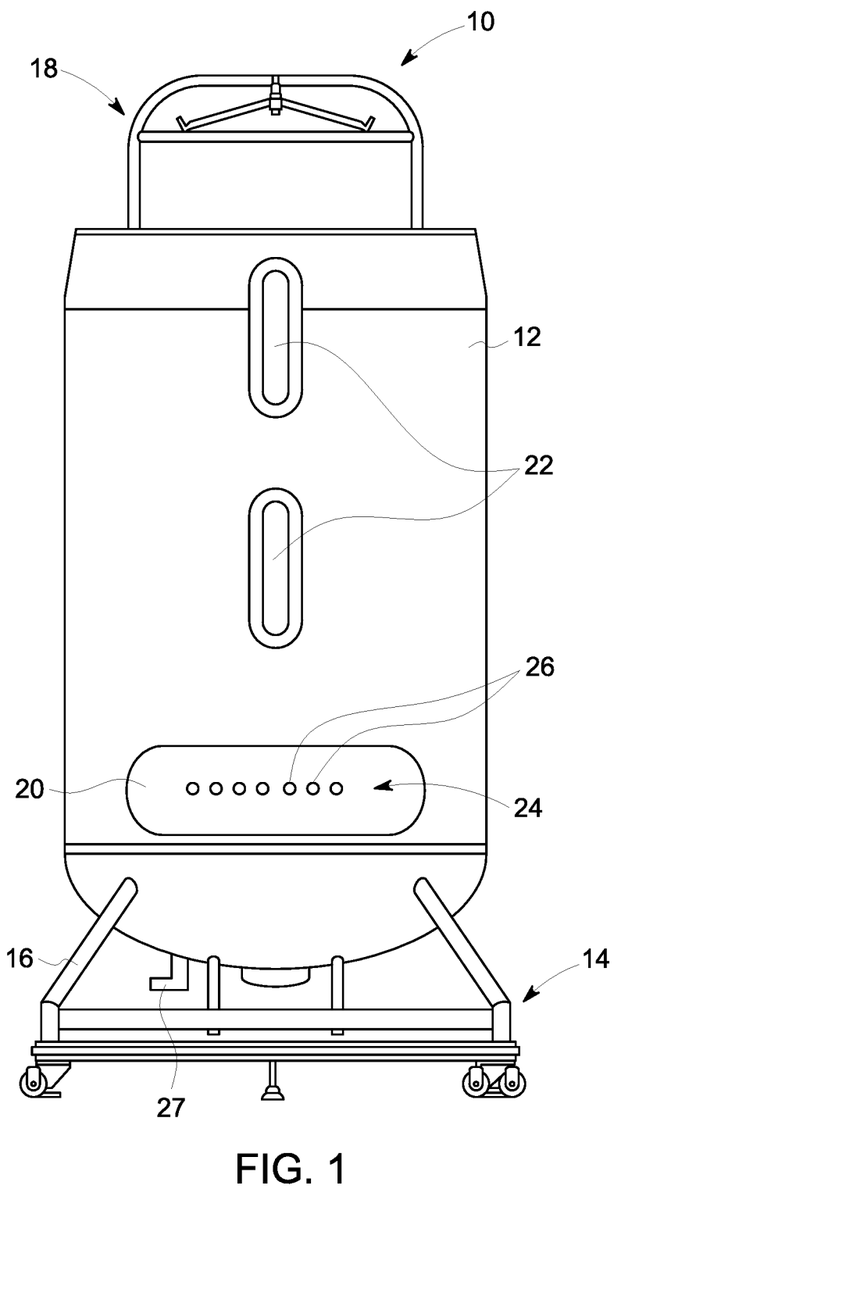
FIG. 1 is a front elevational view of a bioreactor system.
Figure 2:
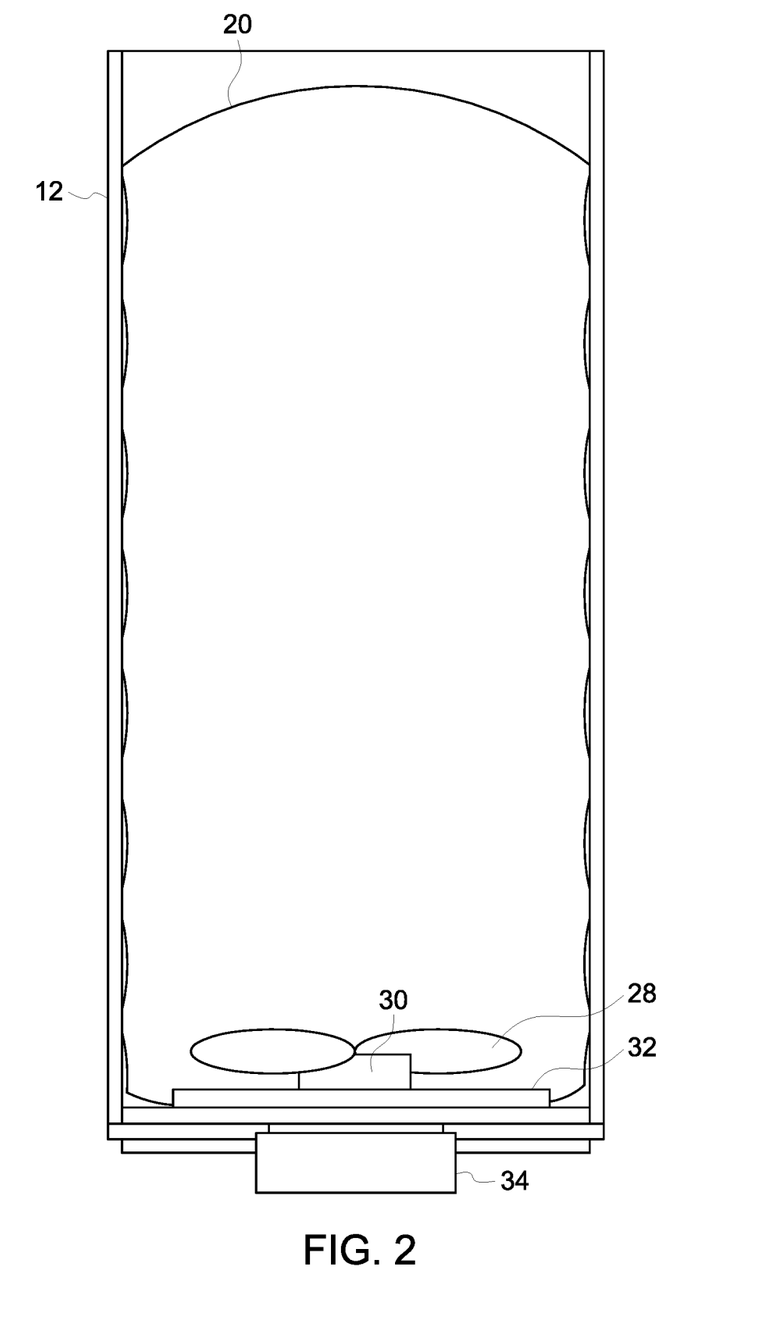
FIG. 2 is a simplified side elevational, cross-sectional view of the bioreactor system of FIG. 1, illustrating a single-use, flexible bioreactor bag in position within a support vessel.

With reference to FIGS. 1 and 2, a bioreactor/bioprocessing system 10 is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift or hanger assembly 18 that provides support to a single-use, flexible bag 20 disposed within the vessel 12. The vessel 12 can be any shape or size as long as it is capable of supporting a single-use flexible bioreactor bag 20. For example, according to one embodiment of the invention the vessel 12 is capable of accepting and supporting a 10-2000L flexible or collapsible bioprocess bag 20.

The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20 and for connecting one or more fluid lines to the flexible bag 20 for fluids, gases, and the like, to be added or withdrawn from the flexible bag 20, e.g., via connector ports 26 extending from the front of the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example. The vessel 12 may also include an aperture in the bottom thereof, through which a drain tube 27 of the bag 20 may extend for selectively draining the contents of the bag 20 after a bioprocessing operation.

With specific reference to FIG. 2, a schematic side elevational, cutaway view of the bioreactor system 10 is illustrated. As shown therein, the single-use, flexible bag 20 is disposed within the vessel 12 and restrained thereby. In embodiments, the single-use, flexible bag 20 is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra-low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. In an embodiment, the flexible material may be a laminate of several different materials such as, for example Fortem™, Bioclear™ 10 and Bioclear 11 laminates, available from GE Healthcare Life Sciences. Portions of the flexible container can comprise a substantially rigid material such as a rigid polymer, for example, high density polyethylene, metal, or glass. The flexible bag may be supplied pre-sterilized, such as using gamma irradiation.

The flexible bag 20 contains an impeller 28 attached to a magnetic hub 30 at the bottom center of the inside of the bag, which rotates on an impeller plate 32 also positioned on the inside bottom of the bag 20. Together, the impeller 28 and hub 30 (and in some embodiments, the impeller plate 32) form an impeller assembly. A magnetic drive 34 external to the vessel 12 provides the motive force for rotating the magnetic hub 30 and impeller 28 to mix the contents of the flexible bag 20. While FIG. 2 illustrates the use of a magnetically-driven impeller, other types of impellers and drive systems are also possible, including top-driven impellers.

As indicated, the pre-sterilized, single-use flexible bags (e.g., bag 20) used in these type of, and similar, bioreactor systems can be large and cumbersome to transport, inspect and install. Accordingly, with reference to FIGS. 3-5, embodiments of the invention provide a packing 100 for such flexible bioprocessing bags (e.g., bioprocessing bag 20). As illustrated therein, the packaging 100 includes a base structure in the for of an open-ended housing 110 formed from a thin, generally rectangular sheet of material such as, for example, corrugated plastic. The housing 110 includes a first panel 112, a second panel 114, a third panel 116, a fourth panel 118 and a fifth panel 120. The first and third panels 112, 116 form opposed lateral sides of the housing 110 and are connected to the second and fourth panels 114, 118, which form the top and bottom of the housing 110, via hinges 122, 124, 126, respectively, as best shown in FIG. 5. As also illustrated therein, the fifth panel 120 is connected to the fourth panel 118 via a hinge 128, and forms an enclosing flap that lies in registration with the first panel 112. As shown therein, the housing 110 is folded about the hinges 122, 124, 126, 128 to form a generally rectangular structure having an open interior space 130 and open opposing ends 132, 134. In an embodiment, the hinges 122, 124, 126, 128 are living hinges that are integral with the adjacent panels, and formed from the same material as the panels. For example, the hinges 122, 124, 126, 128 may be configured as folds or score lines in the housing 110. In such an embodiment, the entire housing 110 may be formed from a generally rectangular sheet of corrugated plastic or other material that is folded about the hinges to form the housing 110.

As best illustrated in FIG. 5, the fifth panel or enclosing flap 120 includes one or more tabs 136, 138 that are folded over and attached (e.g., using an adhesive) to the panel 114 to maintain the rectangular, folded configuration of the housing 110. In another embodiment, the tabs 136, 138 are configured to be received in corresponding slots (not shown) in the first panel 112 (wherein the tabs 136, 138 may be selectively removable from the slots to allow the housing 110 to be open and laid flat). While FIG. 5 illustrates the use of two tabs, more or fewer than two tabs may be utilized. Moreover, it is contemplated that other means may be utilized to selectively maintain the housing 110 in its assembled, rectangular box-like configuration such as, for example, a magnetic coupling between the fifth panel 120 and/or tabs 136, 138 thereof and the second panel 114. Where an adhesive is be utilized, it is configured such that the connection is capable of being broken to allow the housing 110 to be opened and laid flat.

Figure 3:
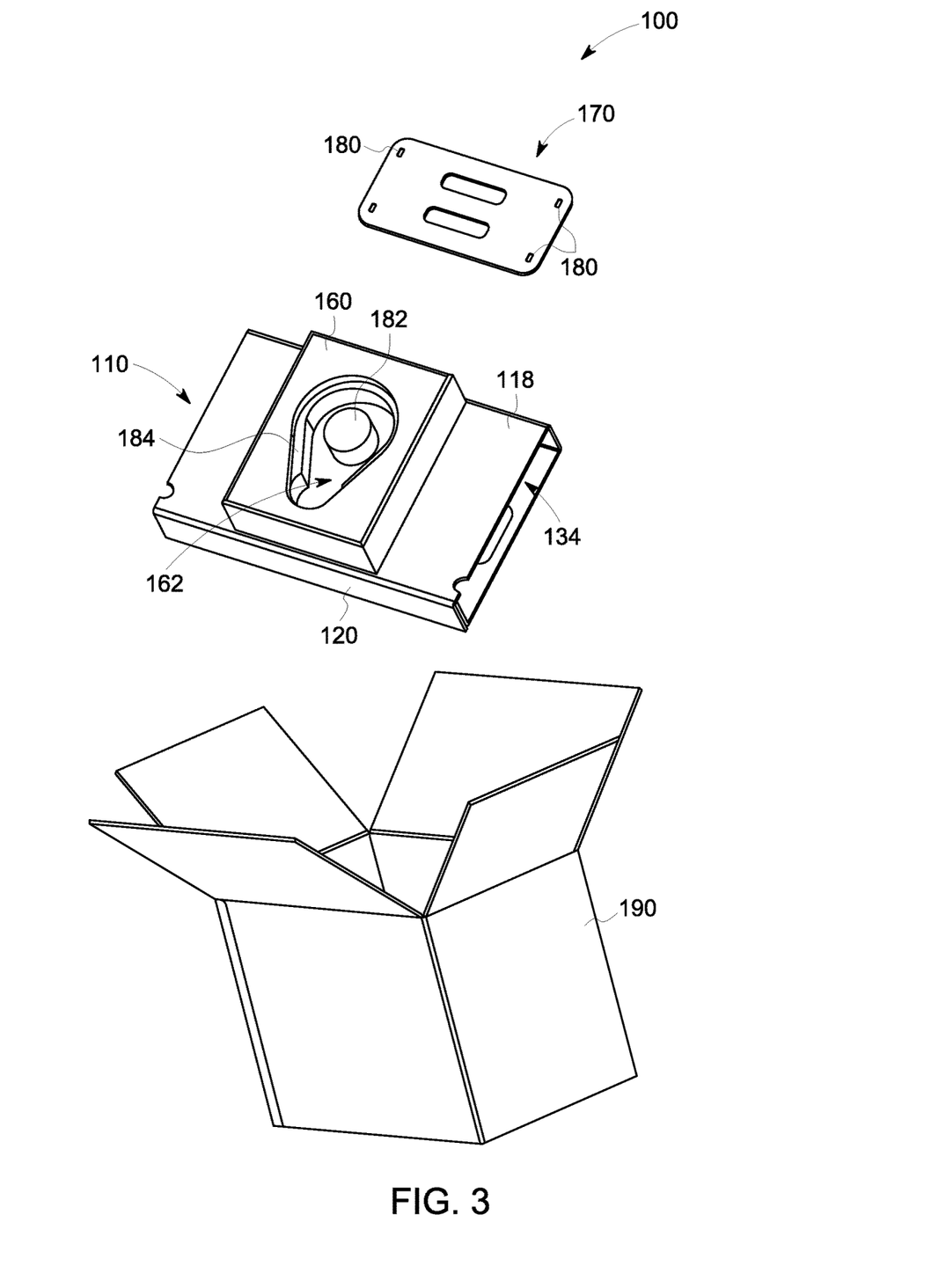
FIG. 3 is perspective view of a packaging for a single-use, flexible bioreactor bag, according to an embodiment of the invention.
Figure 4:
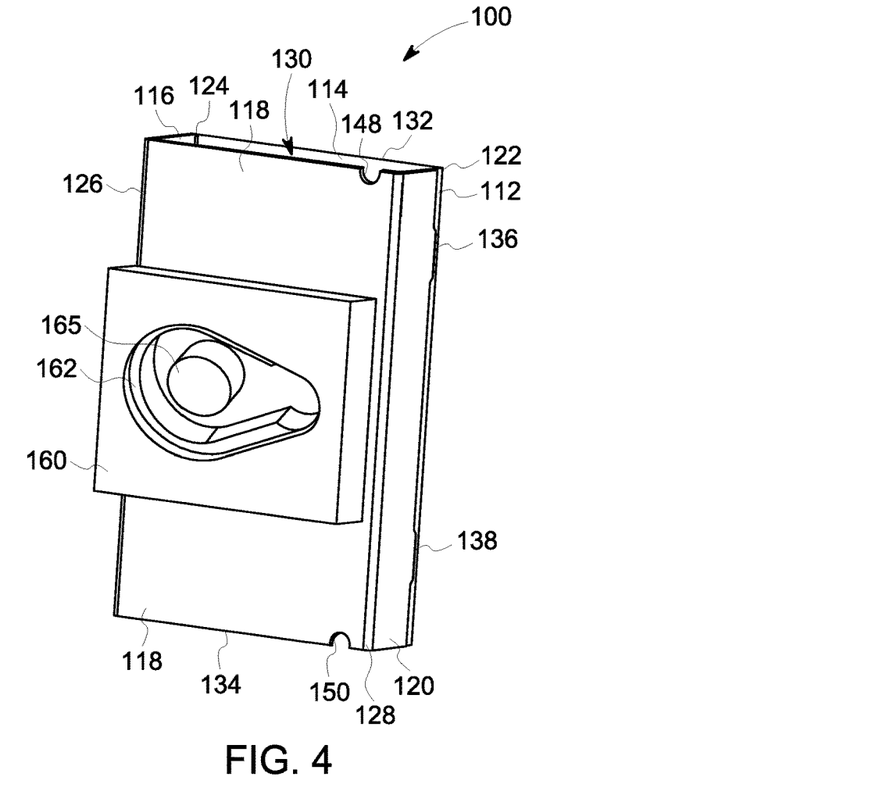
FIG. 4 is another perspective view of the packaging of FIG. 3.
Figure 5:
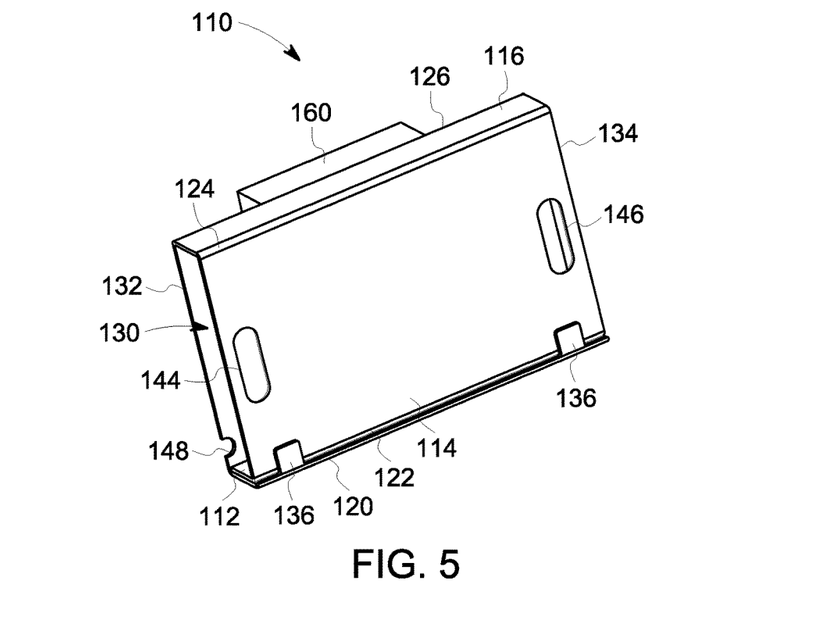
FIG. 5 is another perspective view of the packaging of FIG. 3, showing a reverse side thereof.

As further illustrated in FIGS. 3-5, the second panel 114 may include a pair of cutouts 144, 146 positioned adjacent to opposed ends 132, 134 of the housing 110. The fourth panel 118 may also include a pair of opposed notches 148, 150 in opposed edges thereof, for accommodating tubing of the bioprocessing bag, as discussed hereinafter. Still further, the fourth 118 panel may include a generally rectangular slot or opening 152 arranged at a general midpoint of the panel, adjacent to the hinge 128, which provides a passageway through the panel 118 into the interior space 130, the purpose of which will be described hereinafter.

With additional reference to FIGS. 3-5, the packaging 100 further includes an impeller support base 160 integrally formed with, or otherwise connected to, the external side of the fourth panel 118 of the housing 110. For example, in an embodiment, the base 160 may be affixed to the housing 110 using an adhesive or mechanical interlocking structure. As shown therein, in an embodiment, the base 160 includes a recess 162 that generally corresponds in shape to the impeller base plate (e.g., impeller base plate 32 of FIG. 2) that is positioned inside the flexible bioprocessing bag and atop of which sits the impeller. For example, in an embodiment, the recess 162 may be teardrop shaped.

In an embodiment, the impeller support base 160 includes a central projection 182 that extends upwardly into the recess 162, as well a peripheral flange or shoulder 184 that extends laterally into the recess 162. During packaging, the drain tubing 27 may be coiled around the central projection 182 and positioned within the recess 162, and the impeller base plate 32 may then be positioned in the recess 162 over the drain tubing 27, as discussed hereinafter. In this position, the peripheral flange 184 and/or central projection 182 support the impeller base plate 32 from beneath. The impeller support base 160, therefore, houses and secures the drain tubing 27 and impeller base plate 32 for transport.

In an embodiment the base 160 may be generally rectangular in shape and is formed from a foam material, e.g., a high-density, closed cell foam material. In an embodiment, the high-density, closed cell foam is polymer foam with density 35 kg/m3 or higher, and may be, for example, a polyurethane foam. As described hereinafter, the base 160 is configured to receive the impeller base plate and drain tubing, holding the base plate and impeller in position during transport. In some embodiments, the base 160 may have a central aperture 165.

Figure 6:
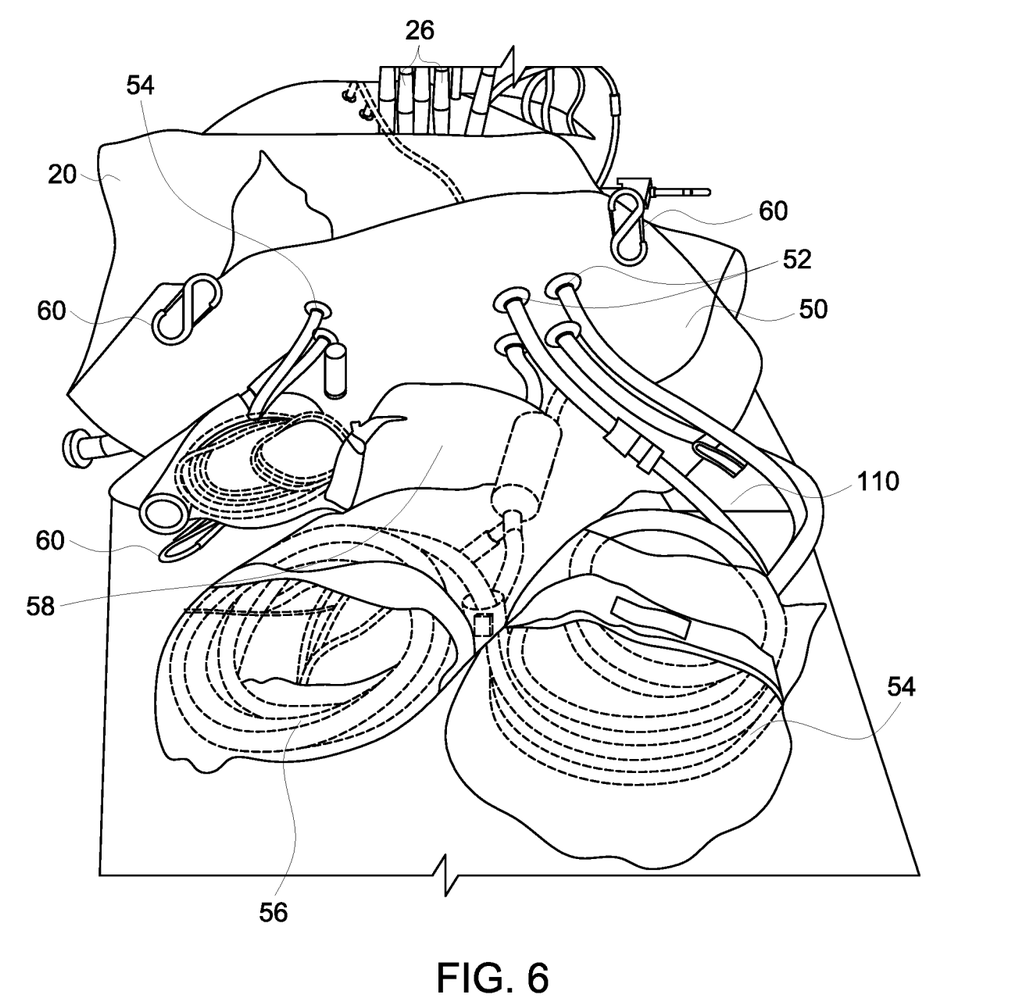
FIG. 6 is a top, perspective view illustrating the bioprocessing bag of FIG. 2 and its associated components.

Turning now to FIGS. 6-13, the manner in which the flexible bioreactor bag 20 is inserted into packaging 100 is illustrated. In an embodiment, the packaging 100 and flexible bioreactor bag 20, and its associated components, collectively, form a kit. As described above, the bag 20 may be outfitted with the array of components and devices described above in connection with FIG. 2 prior to packaging and transport. In addition to the components previously described, the top 50 of the bag 20 may include an array of gas ports 52 and liquid ports 54, to which lengths of tubing are attached, as illustrated in FIG. 6. In an embodiment, the lengths of tubing may be arranged in bundles 54, 56 and wrapped in plastic or bubble wrap for packaging and transport. The bag 20 also includes one or more filters 58, as is known in the art. In an embodiment, the top of the bag 20, when laid flat, forms a pouch or pocket into which the tubing bundles 54, 56 and filters 58 may be inserted. This is perhaps better illustrated in FIG. 7. As further shown in FIG. 6, the top 50 of the bag 20, prior to packaging and transport, is outfitted with a plurality of clips 60 (e.g., four clips) that are utilized to hang the bag 20 from the lift assembly of the bioreactor vessel 10 when inserted therein.

Figure 7:
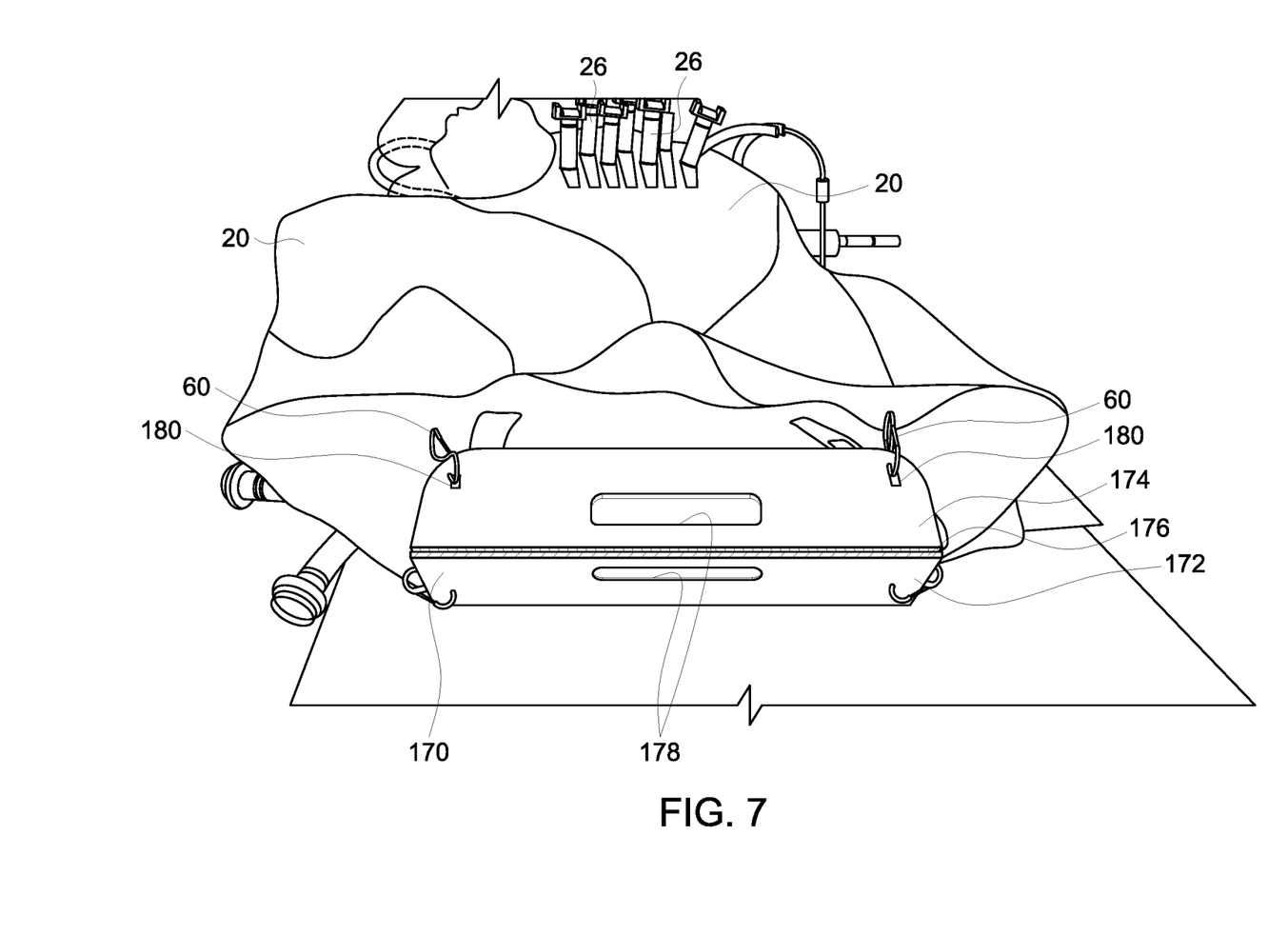
FIG. 7 is another top, perspective view illustrating attachment of a handle to the bioprocessing bag.
Figure 8:
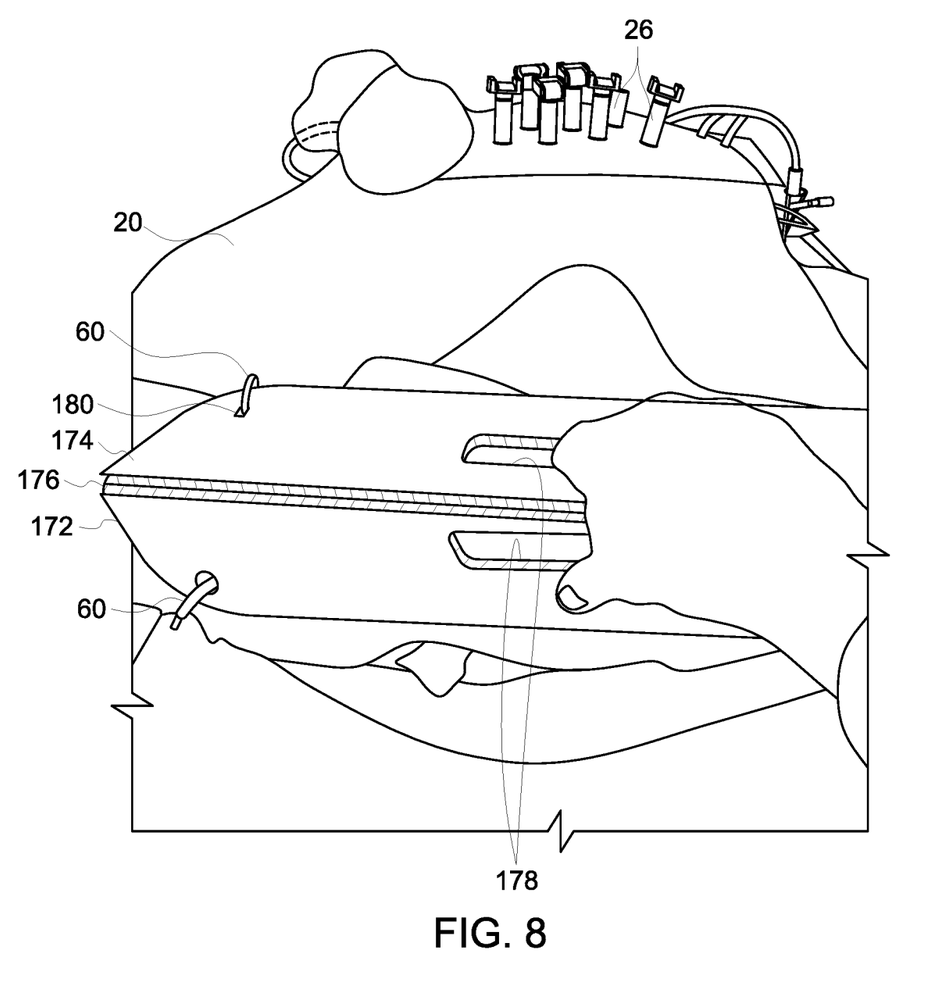
FIG. 8 is a perspective view illustrating grasping of the handle by a user.

As shown in FIG. 7, in an embodiment, the packaging 100 may additionally include a handle 170 made from corrugated plastic or other material, which is separated and apart from the housing 110. The handle 170 may be generally rectangular in shape and has two opposed handle portions 172, 174 separated by a fold or score line 176. Each handle portion 172, 174 includes a slot 178 adjacent to the fold line 176 that is used for grasping the handle 170. Moreover, the handle 170 includes a slot or aperture 180 adjacent to each of the corners thereof, which allows the handle 170 to be coupled to the top 50 of the bag 20 using the clips 60 on the bag 20. As shown in FIG. 2, therefore, once the tubing bundles 54, 56 and filters 58 are positioned within the pouch formed by the top 50 of the bag, the handle 170 is placed over the top 50 of the bag 20 and connected thereto using the clips 60. In this respect, the handle 170 functions to cover the open-end of the pocket formed by the top 50 of the bag 20, retaining the tubing bundles 54, 56 and filters 58 (and any other components connected to the top of the bag) therein. The handle 170 may then be grasped to move the entire bag 20 and its components, as shown in FIG. 8.

Figure 9:
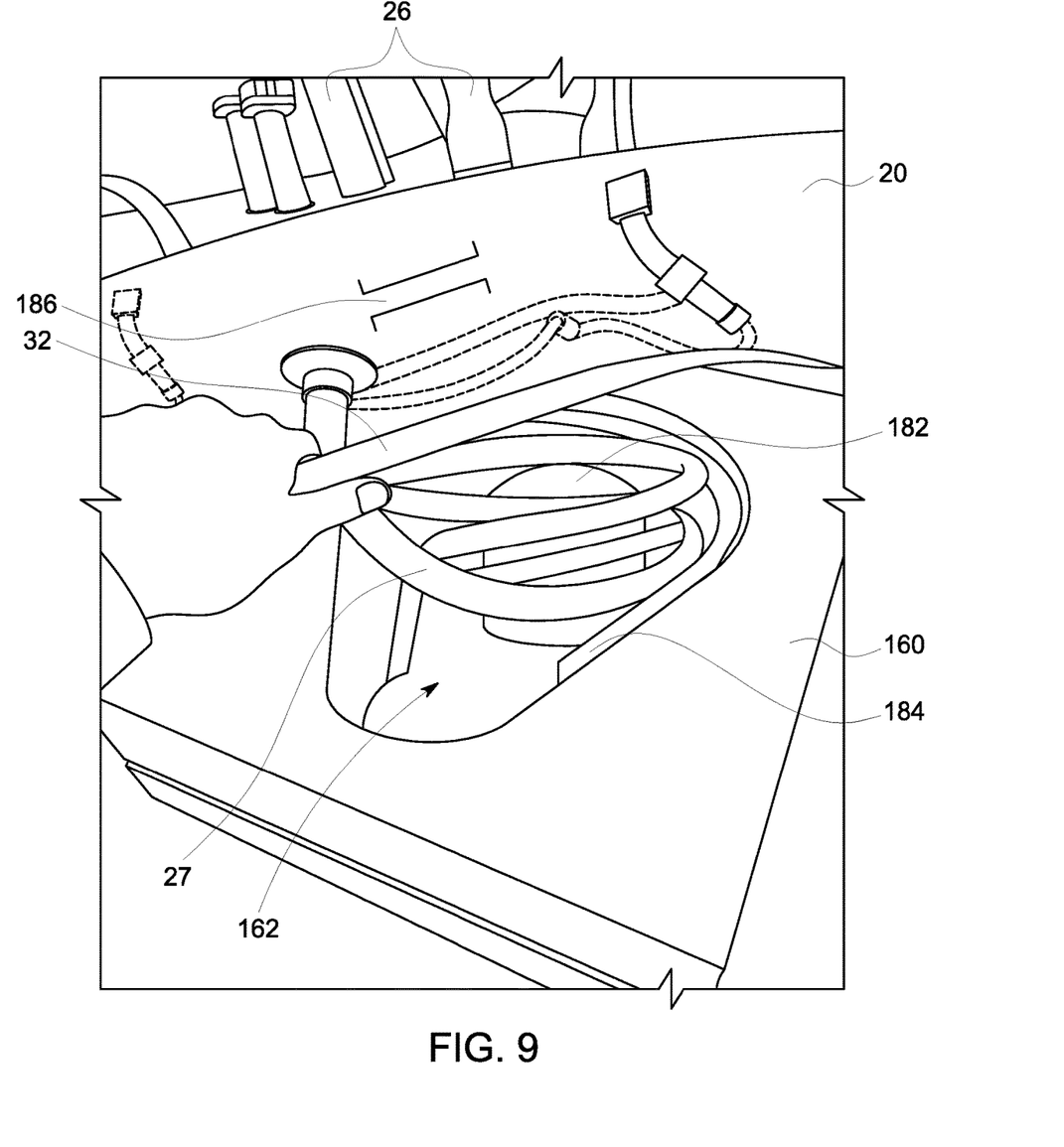
FIG. 9 is an enlarged, perspective view of an impeller support base of the packaging of FIG. 3, illustrating placement of drain tubing and an impeller base plate in the support base.

Turning now to FIG. 9, a bottom of the bioprocessing bag 20 is shown. As illustrated therein, the drain tubing 27 of the bioprocessing bag 27 is coiled and inserted, along with the impeller base plate 32, into the corresponding recess 162 in the impeller support base 160 of the packaging 100. As illustrated in FIG. 9, and as disclosed above, the impeller support base 160 may include a central projection 182 that extends upwardly into the recess 162, as well a peripheral flange 184 that extends laterally into the recess 162. During packaging, the drain tubing 27 may be coiled around the central projection 182 and positioned within the recess 162, and the impeller base plate 32 may then be positioned in the recess 162 over the drain tubing 27. In this position, the peripheral flange 184 and/or central projection 182 support the impeller base plate 32 from beneath. The impeller support base 160, therefore, houses and secures the drain tubing 27 and impeller base plate 32 for transport.

As additionally shown in FIG. 9, the bottom of the bioprocessing bag 20 may include a handle 186 that, together with the handle 170 can be used to lift the bioprocessing bag 20 from the housing 110 and base support 160 so that it can be carried to the bioreactor vessel for installation. In an embodiment, the handle 186 may be integrally formed with the bag 20 (e.g., from the same material as the bag 20).

Figure 10:
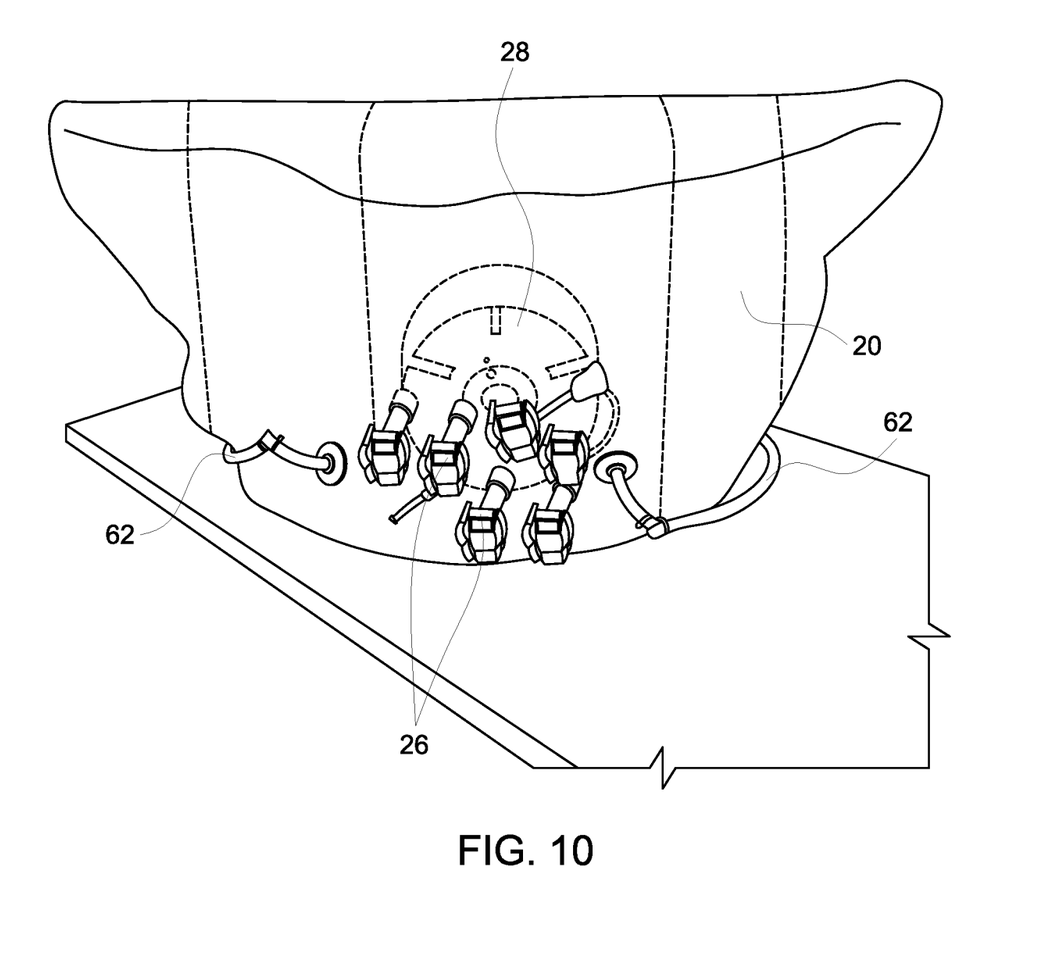
FIG. 10 is a front elevational view of the bioprocessing bag in a partially packaged state.
Figure 11:
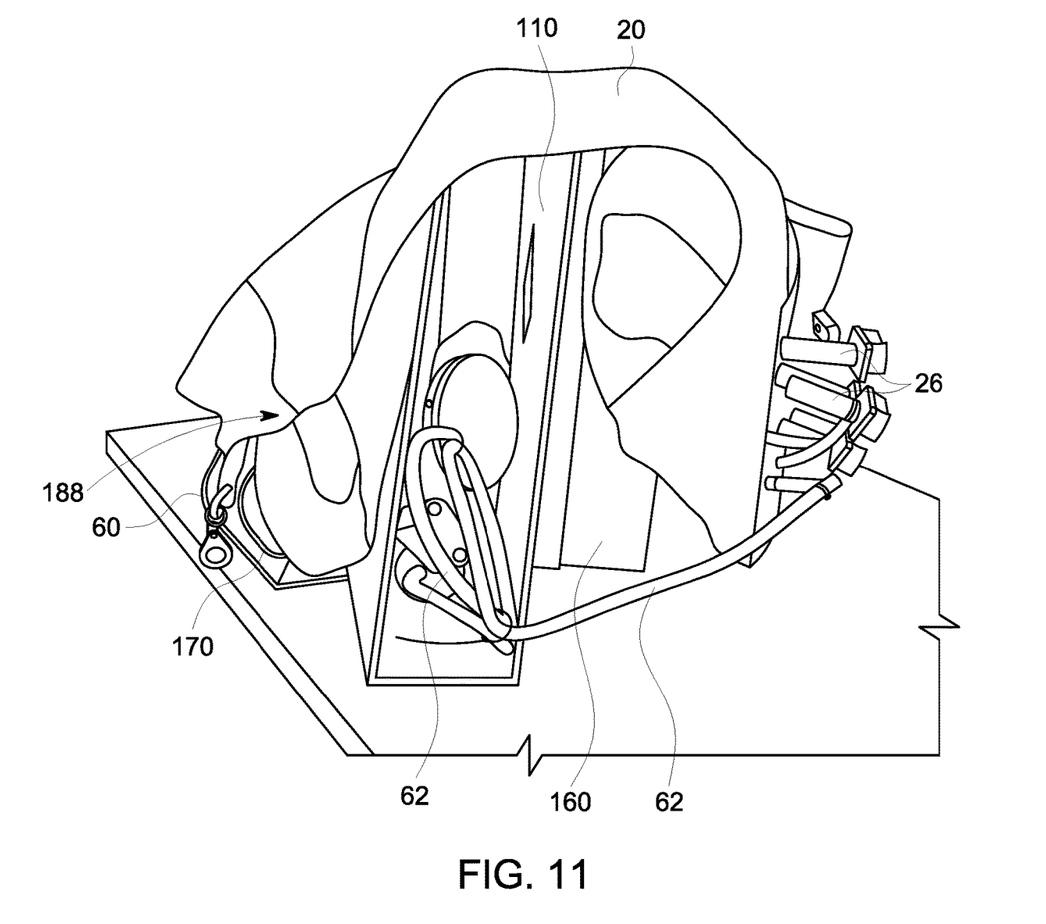
FIG. 11 is a side elevational view of the bioprocessing bag and packaging.
Figure 12:
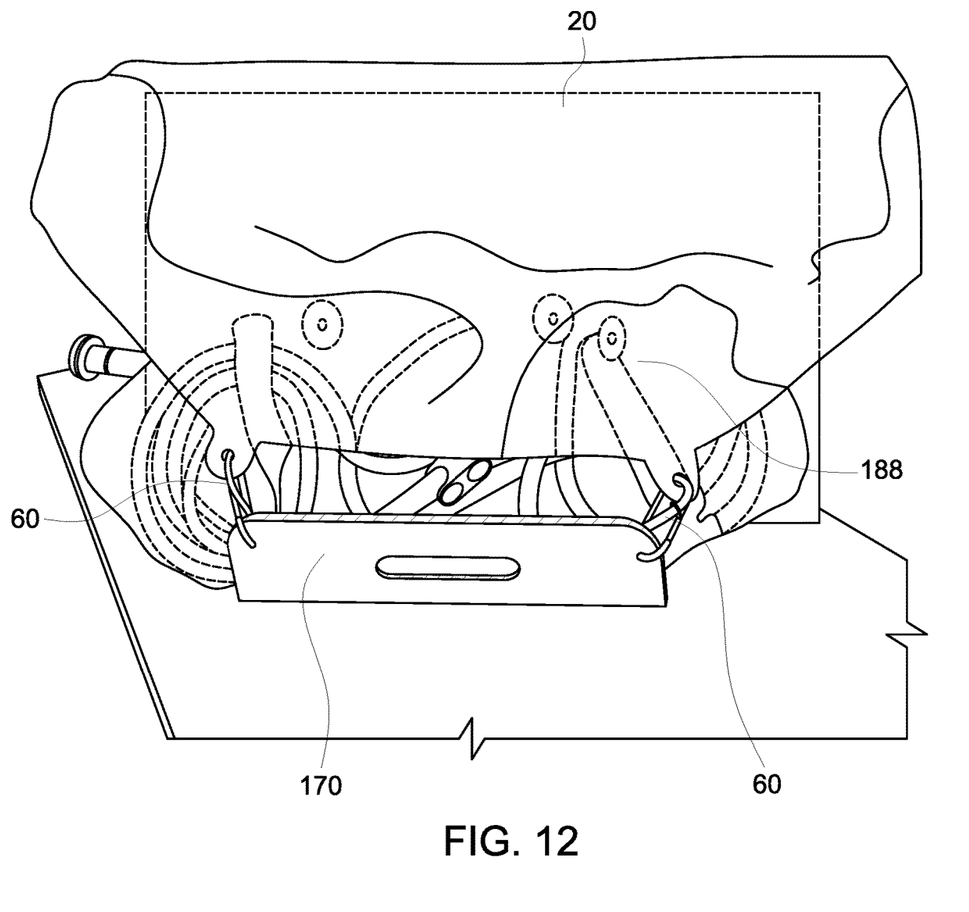
FIG. 12 is a top, perspective view of the bioprocessing bag and packaging.

FIG. 10 shows the bioprocessing bag 20 installed in the packaging 100, with the impeller 28 visible through the front of the bag 20 and the sparge lines 62 extending from the front of the bag. FIG. 11 is a side view showing the packing 100, including housing 110, impeller support base 160 and handle 170 thereof. As shown, the impeller base plate 32 is received in the recess 162 in the support base 160, and the bag 20 is draped over the side 114 of the housing 110. The tubing bundles 54, 56 and filters 58 (and any other components typically present at the top of the bag) are retained in the pocket 188 at the top 50 of the bag, and retained therein by the presence of the handle 170. In this respect, the handle 170 also functions as an enclosing cover, preventing the tubing bundles and other components from moving around during transport. Also, the sparge tubing 62 is coiled and inserted into the interior space 134 of the housing 110. This interior space 134 may also serve to house any additional tubing or components of the bioprocessing bag 20. FIG. 12 shows the kit from the top 50 of the bag 20, in its packaged state. In this position, the sides of the bag 20 may be folded inwards to minimize the volume of the entire package.

Once the bag bioprocessing bag is packaged, as illustrated in FIGS. 11 and 12, it is double-pouched and heat sealed. In particular, the bioprocessing bag 20, housing 110 (including the impeller support base 160) and handle 170 are inserted into a first pouch (not shown), which is sealed shut (e.g., by heat sealing). The first pouch is then inserted into a second pouch (not shown) which is likewise sealed shut (e.g., by heat sealing). After heat-sealing, the kit can be sterilized e.g. by gamma irradiation. In an embodiment, the tubing attached to the bag, and any ports without tubing attached, may be equipped with aseptic connectors to maintain sterility in the interior of the bag when it is installed. This entire package may then be inserted into a box (e.g., box 190 of FIG. 3) for storage and/or transport.

Figure 13:
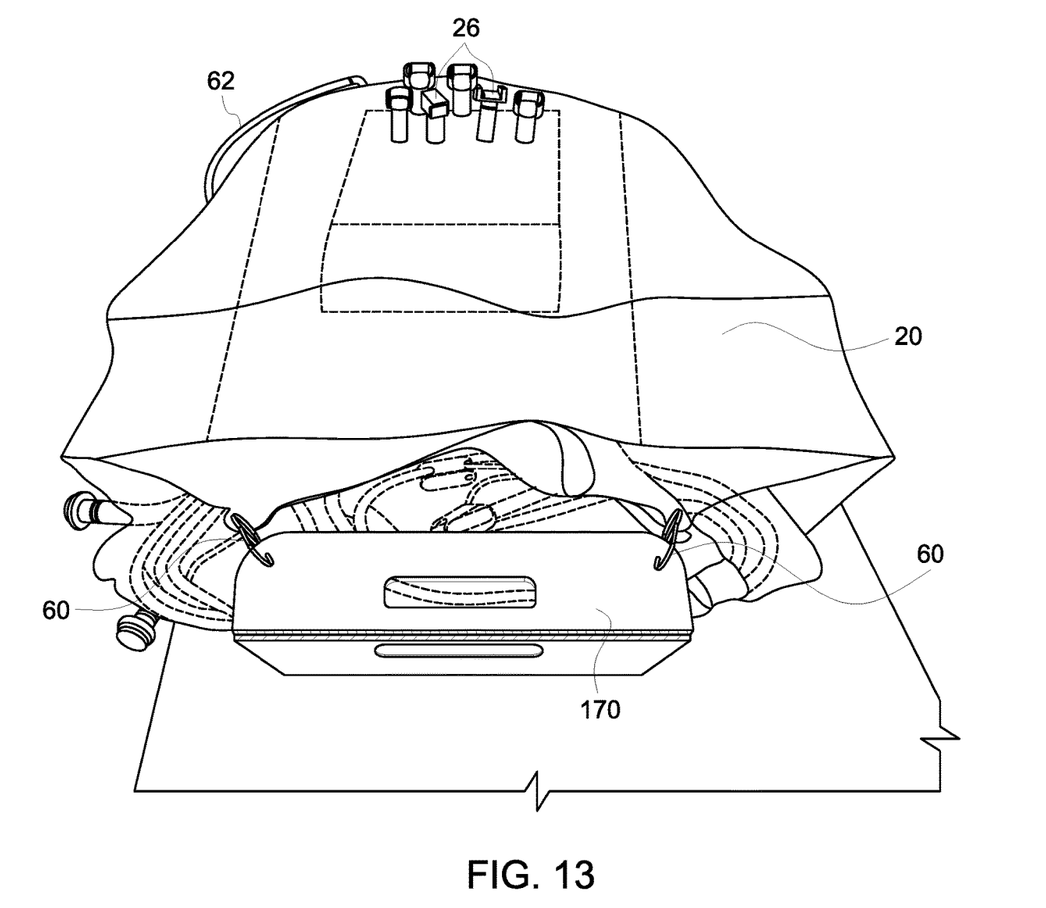
FIG. 13 is a perspective view illustrating a position of the bioprocessing bag for inspection.

With reference to FIG. 13, once the box is 190 is received at a customer's facility, the customer may open the box and remove the bag 20 and packaging 100 from the double pouch. The housing 110 may then be laid flat on a surface by opening the flap 120, causing the bag 20 to also be laid flat on the surface. In this position, the front side of the bag 20 and its associated components can be easily inspected (e.g., for scars, creases, punctures, etc.). The bag 20 can be flipped over by grasping the handle 170 and the bottom of the bag 20 (and/or integral handle 186) so that the back side of the bag 20 can likewise be inspected. Once the bag 20 is inspected, it can be carried to the bioreactor vessel (e.g., vessel 12) using handles 170, 186) installed.

The packaging 100 of the invention minimizes the use of bubble wrap and facilitates inspection of the entire bag and its components prior to installation and use. Moreover, the use of the impeller support base 160 to contain and restrain the impeller base 32 and drain tubing 26 during transport decreases the possibility of damage to the bag during transport, by ensuring that the impeller and magnetic hub do not move around and contact the bag film (that is, it protects the bag film from the impeller). In addition to the above, the packaging 100 and handle 170 thereof provides for easy installation of the bag 20 into the bioreactor vessel, once opened and inspected.

In an embodiment, a packaging for a bioprocessing bag is provided. The packaging includes a housing having an open interior space, and a support base attached to an external side of the housing, the support base having a recess for receiving an impeller base plate of a bioprocessing bag. In an embodiment, the housing includes at least one open end providing access to the open interior space. In an embodiment, the recess of the support base corresponds in shape to a shape of the impeller base plate of the bioprocessing bag. In an embodiment, the packaging further includes a handle configured to attachment to the bioprocessing bag via clips of the bioprocessing bag, wherein the handle is configured for selective decoupling from the bioprocessing bag. In an embodiment, the housing is selectively positionable in a first state, wherein sides of the housing are oriented so as to define the open interior space, and a second state, wherein all sides of the housing lay substantially flat on a surface allowing for inspection of the bioprocessing bag. In an embodiment, the housing is formed from corrugated plastic. In an embodiment, the support base is formed from a high-density, closed-cell foam.

In another embodiment, a kit is provided. The kit includes a flexible bioprocessing bag having an impeller base plate for receiving an impeller, and a packaging having a housing having an open interior space and a support base attached to an external side of the housing. The impeller base plate and drain tubing of the bioprocessing bag are received in a recess in the support base. In an embodiment, the bioprocessing bag includes sparge tubing, wherein the sparge tubing is positioned in the open interior space. In an embodiment, the bioprocessing bag includes a plurality of clips configured to facilitate hanging of the bioprocessing bag from a lift assembly of a bioreactor vessel, and the packaging includes a handle member configured for selective coupling to the bioprocessing bag via the plurality of clips. In an embodiment, the bioprocessing bag includes at least one of gas tubing, liquid tubing and/or filters arranged at a top of the bioprocessing bag, wherein a top of the bioprocessing bag is configured as a pocket for receiving the at least one of gas tubing, liquid tubing and/or filters, and wherein the handle member is configured as a cover to substantially enclose the pocket. In an embodiment, the bioprocessing bag includes an integral handle positioned on, or adjacent to, a bottom of the bioprocessing bag. In an embodiment, at least one of the housing and the handle is formed from corrugated plastic. In an embodiment, the housing is selectively position able in a first state, wherein sides of the housing are oriented so as to define the open interior space, and a second state, wherein all sides of the housing lay substantially flat on a surface allowing for inspection of the bioprocessing bag.

In yet another embodiment, a method of packaging a bioprocessing bag is provided. The method includes the steps of positioning drain tubing and an impeller base plate of a flexible bioprocessing bag in a recess in a support base, the support base being attached to a housing have an open interior space, positioning at least one component of the flexible bioprocessing bag in the open interior space of the housing, and coupling a handle to the flexible bioprocessing bag adjacent to a top of the flexible bioprocessing bag. In an embodiment, the method may further include the step of positioning at least one of tubing and/or a filter in a pouch formed by a top of the flexible bioprocessing bag, wherein the step of coupling the handle to the flexible bioprocessing bag substantially encloses the pouch to retain the at least one of the tubing and/or the filter in the pouch. In an embodiment, the at least one component is sparge tubing of the flexible bioprocessing bag. In an embodiment, coupling the handle to the flexible bioprocessing bag includes connecting a plurality of clips of the bioprocessing bag to the handle, wherein the plurality of clips are configured to facilitate hanging of the bioprocessing bag from a lift assembly of a bioreactor vessel. In an embodiment, the method may further include the step of opening the housing such that the housing lies flat on a surface to facilitate inspection of the flexible bioprocessing bag. In an embodiment, the method also includes the steps of placing the flexible bioprocessing bag, the housing, the support base and the handle in a pouch and heat sealing the pouch.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. In above description, certain directional terms are used, such as "top", "bottom", "left", and "right". Unless otherwise noted, the directional terms are used with respect to the use of the bioreactor shown in the drawings and, in particular, the orientation shown in FIG. 2 of the drawings.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A packaging for a bioprocessing bag, comprising:
a housing comprising a plurality of panels, with one of the panels having an impeller support base plate integrally formed therewith for receiving an impeller base plate of the bioprocessing bag, the impeller support base plate having a protruding portion extending outward from the corresponding panel, the protruding portion having an opening formed therein that exposes an inner region of the protruding portion to define a recess in the impeller support base plate that is bounded by interior wall surfaces of the inner region of the protruding region and a surface of the corresponding panel;
wherein the plurality of panels are configured to be folded, such that the housing forms a box-like configuration.

2. The packaging of claim 1, wherein:
the housing has an interior space that includes at least one open end providing access to an open interior space within the box-like configuration.

3. The packaging of claim 2, wherein:
the housing is selectively positionable in a first state, wherein the plurality of panels of the housing are oriented so as to define the open interior space, and a second state, wherein all of the plurality of panels of the housing lay substantially flat on a surface.

4. The packaging of claim 3, wherein:
the housing is in the form of a sheet of material, the sheet of material including folds or score lines.

5. The packaging of claim 4, wherein:
at least one of the plurality of panels includes one or more tabs, the one or more tabs configured to maintain the box-like configuration.

6. The packaging of claim 1, wherein:
the recess corresponds in shape to a shape of the impeller base plate of the bioprocessing bag.

7. The packaging of claim 6, wherein:
the shape is a teardrop shape.

8. A kit, comprising:
a flexible bioprocessing bag having an impeller base plate for receiving an impeller; and
a packaging having a housing comprising a plurality of panels, with one of the panels having an impeller support base plate integrally formed therewith for receiving the impeller base plate of the flexible bioprocessing bag, the impeller support base plate having a protruding portion extending outward from the corresponding panel, the protruding portion having an opening formed therein that exposes an inner region of the protruding portion to define a recess in the impeller support base plate that is bounded by interior wall surfaces of the inner region of the protruding region and a surface of the corresponding panel;
wherein the plurality of panels are configured to be folded, such that the housing forms a box-like configuration.

9. The kit of claim 8, further comprising:
an interior space within the housing;
wherein, the flexible bioprocessing bag includes sparge tubing; and
wherein the sparge tubing is positioned in the interior space.

10. The kit of claim 8, wherein:
the recess corresponds in shape to a shape of the impeller base plate of the flexible bioprocessing bag.

11. The kit of claim 10, wherein:
the shape is a teardrop shape.

12. The kit of claim 8, wherein:
the housing is selectively positionable in a first state, wherein sides of the housing are oriented so as to define an open interior space, and a second state, wherein all sides of the housing lay substantially flat on a surface allowing for inspection of the flexible bioprocessing bag.

13. The kit of claim 12, wherein:
the housing is in the form of a sheet of material, the sheet of material including folds or score lines.

14. The kit of claim 12, wherein:
at least one of the plurality of panels includes one or more tabs, the one or more tabs configured to maintain the box-like configuration.

15. A method of packaging a flexible bioprocessing bag, comprising the steps of:
providing a housing having a plurality of panels, with one of the panels having an impeller support base plate integrally formed therewith for receiving an impeller base plate of the flexible bioprocessing bag, the impeller support base plate having a protruding portion extending outward from the corresponding panel, the protruding portion having an opening formed therein that exposes an inner region of the protruding portion to define a recess in the impeller support base plate that is bounded by interior wall surfaces of the inner region of the protruding region and a surface of the corresponding panel;
folding the panels to form a box-like configuration with an open interior space;
positioning the impeller base plate of the flexible bioprocessing bag in the recess of the housing;
positioning at least one component of the flexible bioprocessing bag in the open interior space of the housing.

16. The method according to claim 15, wherein:
the recess corresponds in shape to a shape of the impeller base plate of the flexible bioprocessing bag.

17. The method according to claim 16, wherein:
the shape is a teardrop shape.

18. The method according to claim 15, further comprising the steps of:
unfolding the housing such that the housing lies flat on a surface to facilitate inspection of the flexible bioprocessing bag.

* * * * *